United States Patent [19]

Press et al.

[11] Patent Number: 4,880,824
[45] Date of Patent: Nov. 14, 1989

[54] PHENYL AND BENZOYL SUBSTITUTED IMIDAZO-FUSED HETEROCYCLIC CALCIUM CHANNEL BLOCKERS

[75] Inventors: Jeffery B. Press, Rocky Hill; Maud Urbanski, Belle Mead, both of N.J.

[73] Assignee: Ortho Pharmaceutical Corporation, Raritan, N.J.

[21] Appl. No.: 99,417

[22] Filed: Sep. 21, 1987

[51] Int. Cl.[4] .................. A61K 31/425; C07D 513/04; C07D 487/04
[52] U.S. Cl. ..................................... 514/368; 548/154; 548/151; 548/126; 544/184; 544/281; 544/330; 544/350; 568/337; 514/243; 514/249; 514/258; 514/363; 514/366
[58] Field of Search ........................ 548/154; 514/368

[56] References Cited

U.S. PATENT DOCUMENTS

| | | | |
|---|---|---|---|
| 4,103,012 | 7/1978 | Gubin et al. | 424/263 |
| 4,386,092 | 5/1983 | Oe et al. | 424/256 |
| 4,727,145 | 2/1988 | Press et al. | 471/04 |

FOREIGN PATENT DOCUMENTS

| | | | |
|---|---|---|---|
| 112991 | 6/1984 | Japan | 548/154 |

OTHER PUBLICATIONS

Abstract for WO84/167332 (1984).

Yoshitomi Pharmaceutical, Chemical Abstract, vol. 101, No. 151851h (1984).
Burger, *Medicinal Chemistry*, pp. 72–75 (1960).

*Primary Examiner*—Mukund J. Shah
*Assistant Examiner*—E. Bernhardt

[57] ABSTRACT

Heterocyclic compounds of formulae (I) and (II):

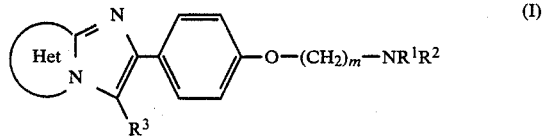

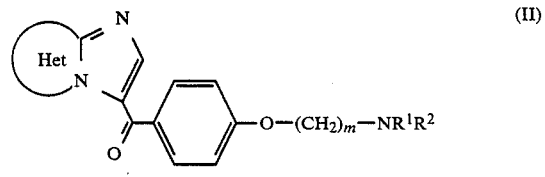

where $R^1$ and $R^2$ are alkyl, $R^3$ is H or alkyl, m is 2–5 and Het is a hetercycle such as thiazole, benzothiazole, substituted benzothiazole, pyrazine, triazine, thiadiazole, substituted thiadiazole, pyrimidine or substituted pyrimidine. The compounds are calcium channel blockers useful in the treatment of cardiovascular conditions such as hypertension or angina.

19 Claims, No Drawings

PHENYL AND BENZOYL SUBSTITUTED IMIDAZO-FUSED HETEROCYCLIC CALCIUM CHANNEL BLOCKERS

BACKGROUND OF THE INVENTION

Thiazoloimidazolyl compounds having an attached phenyl ring which, in turn carries an aminoalkylene group are described in Derwent entry 84-167332/27 for Japanese Pat. No. 59089692.

U.S. Pat. No. 4,386,092 describes fused [3.3.0] and [4.3.0] bycyclic rings having an imidazole as one ring as being useful immunosuppressives. Butoprozine, or p-[3-(dibutylamino)propoxy]phenyl 2-ethyl-3-indolizinyl ketone, is described in U.S. Pat. No. 4,103,012. Imidazo[1,2-a]pyridines are taught in U.S. Ser. No. 909,648 filed Sept. 22, 1986, now U.S. Pat. No. 4,727,145 assigned to the assignee of the present invention.

SUMMARY OF THE INVENTION

Imidazo-fused heterocycles having either a 2-phenyl substituent or a 3-benzoyl substituent are of the following formulae (I) and (II), respectively:

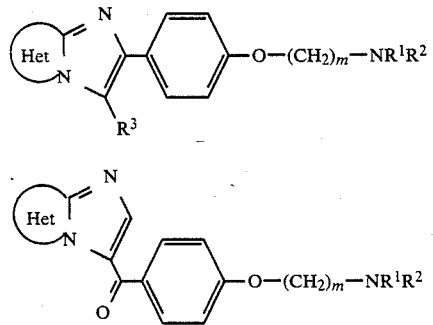

where $R^1$ and $R^2$ are alkyl, $R^3$ is H or alkyl, m is 2–5 and Het represents the atoms necessary for a specified heterocyclic ring which may be substituted. The invention compounds are calcium channel blockers and are useful in the treatment of cardiovascular conditions such as hypertension and angina pectoris.

DETAILED DESCRIPTION OF THE INVENTION

Imidazo-fused heterocyclic compounds of the following formula (I) or (II):

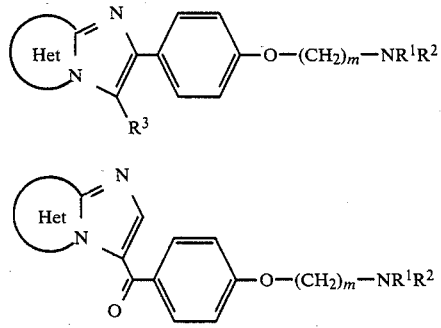

wherein
$R^1$ and $R^2$ are independently alkyl;
$R^3$ is hydrogen or alkyl;

m is an integer from 2 to 5; and
Het represents the atoms necessary to form a heterocyclic ring selected from the group consisting of thiazole, benzothiazole, benzothiazole independently substituted by halo, alkoxy, alkyl or hydroxy, a pyrazine, a triazine, a thiadiazole, a thiadiazole substituted by alkyl, a pyrimidine, or a pyrimidine independently substituted by halo, alkoxy, alkyl or hydroxy,
and the pharmaceutically acceptable acid-addition salts thereof.

In more detail, $R^1$ and $R^2$ are independently alkyl of about 1 to 5 carbons, e.g. methyl, ethyl, n-butyl and 3-methyl-n-butyl; $R^3$ is hydrogen or alkyl of about 1 to 5 carbons, e.g. methyl, ethyl, n-butyl and 3-methyl-n-butyl; m is 2, 3, 4 or 5; and Het represents the atoms necessary to form a thiazole; benzothiazole; benzothiazole independently substituted by one or more, preferably 1 to 2, of halo, e.g. fluoro, chloro, bromo or iodo, alkoxy, e.g. of about 1 to 5 carbons such as methoxy or iso-propoxy, alkyl, e.g. of about 1 to 5 carbons such as methyl, ethyl or tert-butyl, or hydroxy; a pyrazine, e.g. 2-amino-pyrazine; a triazine, e.g. a 1,2,3-triazole, a 1,2,4-triazine or a 1,3,5-triazine; a thiadiazole, e.g. a 1,2,4- or 1,3,4-thiadiazole; a thiadiazole substituted on an open carbon by alkyl, e.g. of about 1 to 5 carbons; a pyrimidine; or a pyrimidine independently substituted by one or more of halo, e.g. fluoro, chloro, bromo or iodo, alkoxy, e.g. of about 1 to 5 carbons such as methoxy, ethoxy or sec-butoxy, alkyl, e.g. of about 1 to 5 carbons such as methyl, ethyl or iso-butyl, or hydroxy.

Representative salts of the compounds of formulae (I) and (II) which may be used include those made with acids such as hydrochloric, hydrobromic, hydroiodic, perchloric, sulfuric, nitric, a phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluene sulfonic, cyclohexanesulfamic, salicylic, p-aminosalicylic, 2-phenoxybenzoic, 2-acetoxybenzoic or a salt made with saccharin. Such salts can be made by reacting the free base of (I) or (II) with the acid and recovering the salt.

Particular compounds of the invention include the following:
6-(4-dibutylaminopropoxyphenyl)-2-methylimidazo[2,1b]-1,3,4-thiadiazole
6-(4-dibutylaminopropoxyphenyl)imidazo[2,1-b]thiazole
6-(4-dibutylaminopropoxyphenyl)-5-methylimidazo[2,1-b]thiazole
3-(4-dibutylaminopropoxyphenyl)imidazo[2,1-b]benzothiazole
2-(4-dibutylaminopropoxyphenyl)imidazo[1,2-b]-1,2,4-triazine
2-(4-dibutylaminopropoxyphenyl)imidazo[1,2-a]pyrimidine
2-(4-dibutylaminopropoxyphenyl)-7-methylimidazo[1,2-a]pyrimidine
3-(4-dibutylaminopropoxybenzoyl)imidazo[1,2-a]pyrimidine
3-(4-dibutylaminopropoxybenzoyl)-7-methylimidazo[1,2-a]pyrimidine As used herein, "independently" refers to the independent choice of substituents when more than one is attached, e.g. the pyrimidine substitutions may be chloro and methoxy since the substitution is defined as being independently chosen from halo, alkoxy, alkyl or hydroxy. "Alkyl" groups herein are either straight or branched unless indicated otherwise. The invention definition of formulae (I) and (II) includes racemates and individual isomers, e.g. as caused by the presence of an asymmetric carbon such as when R¹ would be sec-butyl. Also within the scope of the invention are compounds of the invention in the form of hydrates and other solvate forms.

To prepare invention compounds of formula (I), one may proceed via the following Method I:

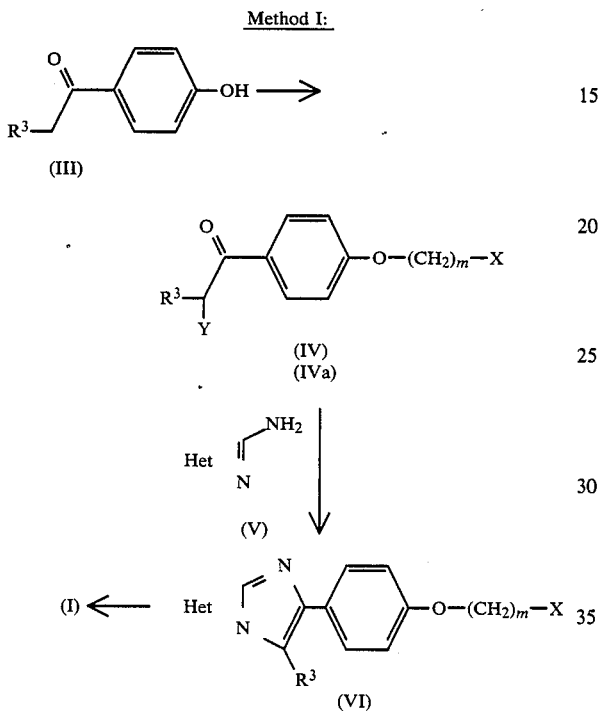

In Method I, a p-hydroxyacetophenone of formula (III) where $R^3$ is as defined for Formula (I), is treated with a 1-bromo-omega-chloroalkane such as 1-bromo-2-chloroethane, 1-bromo-3-chloropropane, 1-bromo-4-chlorobutane or 1-bromo-5-chloropentane in an alcoholic base such as methanolic potassium hydroxide at 60°–85° C. for about 12–48 hr to produce a p-chloroalkoxyacetophenone of formula (IV) where X is Cl and Y is H. The phenone of formula (IV) is then reacted with bromine in any of an ether solvent such as THF or Et₂O, glacial acetic acid or carbon disulfide at 10°–65° C. for 2–24 hr to give the α-bromoketone of formula (IVa) where X is Cl and Y is Br. Condensation of (IVa) with various amino substituted nitrogen heterocycles of formula (V), where Het is as defined for formulae (I) and (II), in either an alcoholic solvent such as MeOH, EtOH or isopropanol or in acetone at about 20°–85° C. yields the product (VI) where Het, $R^3$ and m are defined for formulae (I) and (II) and X is Cl. Specific examples of the amine (V) include 2-aminothiazole, 3-amino-1,2,4-triazine, 3-amino-1,2,4-triazine, 2-amino-1,3,4-thiadiazole, 2-aminopyrazine, 4-aminopyrimidine, 2-aminopyrimidine, 2-amino-4-methylpyrimidine, 2-amino-4-methylthiazole, 2-amino-4-hydroxy-6-methylpyrimidine, 2-amino-4,6-dimethylpyrimidine, 2-aminobenzothiazole and 2-amino-4-chloro-6-methylpyrimidine.

The intermediate (V) is converted to the invention product of formula (I) by treatment in an amine solvent such as dimethylamine, diethylamine, dipropylamine, dibutylamine or dipentylamine at about 100°–150° C. for 6 to 64 hr.

To prepare invention compounds of formula (II), one may proceed via the following Method (II):

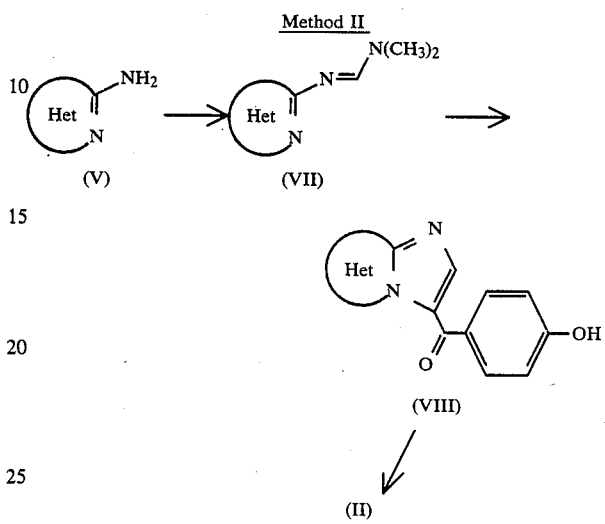

In Method II, an amino substituted heterocycle of formula (V) where Het is as defined for formulae (I) and (II) is treated with dimethylformamide dimethylacetal or triethyl orthoformate in an inert solvent such as benzene, toluene or xylenes or in acetone at 60° to 120° C. for 2 to 12 hr to form the amidines (VII) where Het is as defined for formulae (I) and (II). Examples of the heterocycle (V) include 2-aminothiazole, 3-amino-1,2,4-triazine, 3-amino-1,2,4-triazine, 2-amino-1,3,4-thiadiazole, 2-aminopyrazine, 4-aminopyrimidine, 2-aminopyrimidine, 2-amino-4-methylpyrimidine, 2-amino-4-methylthiazole, 2-amino-4-hydroxy-6-methylpyrimidine, 2-amino-4,6-dimethylpyrimidine, 2-aminobenzothiazole and 2-amino-4-chloro-6-methylpyrimidine.

The amidine (VII) is then condensed with p-hydroxy-2-bromoacetophenone to yield the phenol (VIII) by reaction in an alcohol such as MeOH, EtOH or isopropanol at 60° to 85° C. for 2 to 24 hr. The p-hydroxy-2-bromoacetophenone is prepared by brominating p-hydroxyacetophenone in a manner as described in Method I. The phenol (VIII) is then reacted with a compund of the formula Cl—(CH₂)ₘ—NR¹R² in an alcoholic base such as KOH in MeOH with or without the presence of catalytic iodide at about 60° to 85° C.

The compound of formula Cl—(CH₂)ₘ—NR¹R² is prepared by treating Cl—(CH₂)ₘ—Br with HNR¹R² at about 100° to 150° C.

Nitrendipine Binding Assay (NBA)

The NBA is performed on female, New Zealand white rabbits (1–2 kg) which are sacrificed by cervical dislocation. The heart is immediately removed, cleaned and chopped into small pieces. The tissue is homogenized in 5X volume of 0.05M Hepes buffer, pH 7.4. The homogenate is centrifuged at 4000×g for 10 min; the supernatant is recentrifuged at 42,000×g for 90 min. The resulting membrane pellet is resuspended (0.7 ml/g weight in 0.05M Hepes, pH 7.4 and stored at −70° C. until used. Each tube of the binding assay contains ³H- nitrendipine (0.05–0.50nM), buffer, membranes (0.10mL), and test compound in a total volume of 1.0 mL. After 90 min at 4° C., the bound nitrendipine is separated from the unbound by filtration on Whatman GF/C fibers. After rinsing, the filters are dried and counted in a liquid scintillation counter.

Non-specific binding of $^3$H-nitrendipine (that amount bound in the presence of excess unlabelled nitrendipine) is subtracted from the total bound to obtain specifically bound radiolabeled nitrendipine. The amount of specifically bound nitrendipine in the presence of a test compound is compared to that amount bound in the absence of a compound. A percent displacement (or inhibition) can then be obtained.

Inhibition of Calcium Dependent Smooth Muscle Contraction (ICDSMC)

The inhibition of calcium dependent smooth muscle contraction is measured with the trachea from dogs sacrificed by excess KCl injection and stored overnight at 4° C. in oxygenated Krebs-Henseleit buffer. Tracheal rings, one cartilage segment wide (5–10 mm), are cut starting from the bronchial end. After cutting the cartilage, the trachealis muscle tissue is suspended in oxygenated Krebs-Henseleit buffer at 37° C. in a 25 mL tissue bath. After a 60 min equilibration period, the tissues are challenged with 10 µM carbachol. After 5 min the tissues are rinsed and allowed to rest 50 min. The tissues are then challenged with 50 mM KCl and after 30 min, the contractions are quantitated. The tissues are then rinsed and reequilibrated for 50 min. Test compounds are then added for 10 min, and the tissue is rechallenged with 50 mM KCl. After 30 min, the contraction is recorded and used to determine the % inhibition of control.

The percent inhibition of smooth muscle contraction is calculated from response data before and after drug treatment according to the following equation.

$$\% \text{ inhibition} = 100 - 100 \frac{\text{(peak response after drug treatment)}}{\text{peak response before drug treatment}}$$

Calcium channel blockers have utility as antihypertensive agents (Isr. J. Med. Sci., 18, 735 (1982)), peripheral vasodilating agents (West. J. Med., 137, 24 (1982)) and skeletal smooth muscle relaxants (Progress in Pharmacology, 5, 1 (1982)). Calcium plays a vital role to the function of cardiac tissue and vascular smooth muscle (Annual Reports in Med. Chem., 16, 257 (1981)). Smooth muscle contraction is influenced by the intracellular influx of calcium ions (Ann. Rev. Pharmacol. Toxicol, 17, 149 (1977)). Calcium channel blockers inhibit the influx of extracellular calcium into cells through the slow channel in the cell membrane (Annual Reports in Med. Chem, 16, 257 (1981)). The affect of this blockade leads to an increase in the heart's blood supply by reducing the spontaneous constriction of cardiac and arterial muscle cells (JAMA, 247, 1911 (1982)).

By establishing the test results for a compound of the invention in the NBA and ICDSMC, one can determine which activity, between antihypertensive and vasodilating, is more pronounced in the particular compound.

When used as an antihypertensive agent, a compound of the invention may be used in a manner similar to prazosin or diltiazem and may be administered in an amount of about 0.1 to 10 mg per kg of body weight of the mammal to be treated per day, e.g. about 0.1 to 0.3 mg/kg. The activity of the particular compound and the degree of hypertension in the individual will affect the precise dose as will be determined by a physician skilled in the art.

When used as a vasodilator, the activity of the particular compound and the degree of angina in the individual will affect the precise dose as will be determined by a physician skilled in the aart.

To prepare the pharmaceutical composition of this invention, one or more compounds or salt thereof of the invention as the active ingredient, is intimately admixed with a pharmaceutical carrier according to conventional pharmaceutical compounding techniques, which carrier may take a wide variety of forms depending on the form of preparation desired for administration, e.g. oral or parenteral. In preparing the compositions in oral dosage form, any of the usual pharmaceutical media may be employed. Thus, for liquid oral preparation, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by stnadard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g. tablet, capsule, powder injection, teaspoonful and the like, from about 1 to about 500 mg of the active ingredient, and, preferably, from about 10 to about 100 mg.

Test results for compounds of the present invention in the NDA and ICDSMC are shown in Table I wherein for compounds of formula (I) and (II), Het is an shown, R$^1$ and R$^2$ are n-butyl, m is 3 and R$^3$ is hydrogen, except for Example 3 where R$^3$ is methyl.

TABLE I

| Het | Formula | Example | NBA | ICDSMC |
|---|---|---|---|---|
| CH$_3$—(S,N,N thiadiazole) | (I) | 1d | IC$_{50}$ = 1.1 µM | 82% @ 10 µM<br>50% @ 1 µM<br>27% @ 5 µM |

TABLE I-continued

| Het | Formula | Example | NBA | ICDSMC |
|---|---|---|---|---|
| (thiophene-CH(CH3)-N(CH3)- structure) | (I) | 2 | IC$_{50}$ = 1.5 μM | 81% @ 20 μM<br>55% @ 10 μM<br>24% @ 2 μM<br>28% @ 1 μM |
| (thiophene-CH(CH3)-N(CH3)- structure) | (I) | 3 | IC$_{50}$ = 1.3 μM | 75% @ 10 μM<br>11% @ 1 μM |
| (benzothiophene structure) | (I) | 4 | IC$_{50}$ = 3.1 μM | 38% @ 20 μM |
| (pyridazine structure) | (I) | 5 | IC$_{50}$ = .6 μM | 85% @ 20 μM<br>45% @ 10 μM |
| (pyrazine structure) | (I) | 6 | 43% @ 68 μM | 65% @ 20 μM<br>46% @ 10 μM<br>26% @ 2 μM |
| (methyl-pyrimidine structure) | (I) | 7 | — | 25% @ 2 μM<br>39% @ 10 μM |
| (pyrimidine structure) | (II) | 8c | IC$_{50}$ = 7.0 μM | 70% @ 1 μM<br>60% @ .5 μM<br>37% @ .1 μM |
| (methyl-pyrimidine structure) | (II) | 9b | — | 19% @ 10 μM |

Also part of the present invention are methods of preparing compounds of formulae (I) and (II), novel intermediates and pharmacetical composition and methods.

In the following Examples, the following abbreviations are used: E (trans); Z (cis); bp (boiling point); mp (melting point); g (grams); mL (milliliters); glc (gas liquid chromatography); hplc (high pressure liquid chromatography); NMR (nuclear magnetic resonance); EA (elemental analysis); N (normal); M (molar); nM (nanomolar); μM (micromolar); THF (tetrahydrofuran); MeOH (methanol); DMF (N,N-dimethylformamide); DMPU (1,3-dimethyl-3,4,5,6-tetrahydro-2(1H)pyrimidine); LDA (lithium diisopropylamide); Ac (acetyl, CH$_3$CO—); RT (room temperature); DME (1,2-dimethoxyethane); DMSO (dimethylsulfoxide); EtOH (ethanol); HMPA (hexamethylphosphoramide); mmol (millimoles); mg (milligrams); mm (millimeters); hr (hours); min (minutes); d (doublet); Hz (Hertz); t (triplet); m (multiplet); and C, H, N, etc. (the chemical symbols for the elements). Unless otherwise indicated, all temperatures are reported in degrees centigrade (°C.), all pressures in mm of mercury and all references to ether are to diethyl ether.

EXAMPLE 1 a. 4-(3-Chloro)propoxyacetophenone

To a mixture of p-hydroxyacetophenone (50.7 g, 0.37 m) and 1-bromo-3-chloropropane (160 mL, 1.5 mol) in MeOH (250 mL) was added portionwise potassium hydroxide (63 g, 1.12 mol). The mixture was sitrred at reflux for 24 hr, cooled to RT, filtered through Celite and evaporated in vacuo. The residual semi-solid was diluted with Et$_2$O (500 mL) and washed with H$_2$O (2×300 mL). The ether solution was dried over MgSO$_4$, filtered and evaporated in vacuo to give the title product as a liquid in 68% yield (53.3 g).

$^1$H NMR (CDCl$_3$): δ 7.98–7.89 (d, J=8.9 Hz, 2H), 7.02–6.92 (d, J=8.9 Hz, 2H), 4.16 (t, J=5.9 Hz, 2H), 3.75 (t, J=6.4 Hz, 2H), 2.52 (s, 3H), 2.34–2.16 (m, 2H).

b. α-Bromo-4-(3-chloro)propoxyacetophenone

To a stirred solution of the product of Example 1a (53.3 g, 0.25 mol) in Et$_2$O (250 mL) was slowly added bromine (13 mL, 0.25 mol) and the mixture was allowed to stir at RT for 16 hr. The dark mixture was poured into an aqueous saturated sodium bicarbonate solution (300 mL) and the organic layer separated. The ether layer was washed with an aqueous saturated sodium bicarbonate solution (300 mL) and with water (300 mL) and dried over MgSO$_4$. The solution was filtered and evaporated in vacuo to yield the title product (64.4 g, 88%) as a dark oil.

$^1$H NMR (CDCl$_3$): δ 7.96 (d, J=8.9 Hz, 2H), 6.95 (d, J=8.9 Hz, 2H), 4.41 (s, 2H), 4.19 (t, 2H), 3.75 (t, 2H), 2.26 (M, 2H).

c. 6-(4-Chloropropoxyphenyl)-2-methylimidazo[2,1-b]-1,3,4-thiadiazole

A mixture of the product of Example 1b (10 g, 34 mmol) and 2-amino-5-methyl-1,3,4-thiadiazole (3.9 g, 34 mmol) in EtOH (100 mL) was stirred at reflux for 5 hr. The mixture was cooled to RT, the resulting precipitate was collected by filtration and washed with cold EtOH to give the title product (11.4 g, 86%) as an off-white solid.

$^1$H NMR (CD$_3$OD): δ 8.06 (d, J=8.7 Hz, 2H), 7.12 (d, J=8.7 Hz, 2H), 5.85 (s, 1H), 4.24 (t, J=4.5 Hz, 2H), 3.77 (t, J=4.7 Hz, 2H), 2.59 (s, 3H), 2.26 (m, 2H).

d. 6-(4-Dibutylaminopropoxyphenyl)-2-methylimidazo[2,1-b]-1,3,4-thiadiazole dihydrochloride (Formula I: Het=5-methyl-1,3,4-thiadiazole; R$^1$,R$^2$=(CH$_2$)$_3$CH$_3$; m=3; R$^3$=H)

To a mixture of the product of Example 1c (3.2 g, 8.2 mmol) in DMSO (40 mL) was added dibutylamine (10 mL). The solution was stirred at reflux for 6 hr, cooled to RT, poured into H$_2$O (200 mL) and extracted with CH$_2$Cl$_2$ (1×200 mL). The organic layer was dried over MgSO$_4$, filtered and concentrated. The resulting oil was flash chromatographed (SiGel 60, 9:1 CH$_2$Cl$_2$—MeOH) to give the free base of the title compound. The HCl salt was prepared by dropwise addition of concentrated hydrochloric acid to a solution of the free base in MeOH, concentrated and recrystallized from acetone to yield 1.5 g (39%) of the title product as a white solid, mp 163°–166° C.

EA: Calculated for C$_{22}$H$_{32}$N$_4$OS.2HCl.H$_2$O: C, 53.75; H, 7.38; N, 11.40 Found: C, 53.22; H, 7.60; N, 11.37

EXAMPLE 2

6-(4-Dibutylaminopropoxyphenyl)imidazo[2,1-b]thiazole dihydrochloride (Formula I: Het=thiazole; R$^1$,R$^2$=(CH$_2$)$_3$CH$_3$; m=3; R$^3$=H)

The title compound was prepared in two steps as described in Example 1c and 1d starting with 2-aminothiazole (2.23 g, 23 mmol) in the place of 2-amino-5-methyl-1,3,4-thiadiazole, through 6-(4-chloropropoxyphenyl)imidazo-[2,1-b]thiazole to produce 1.2 g (83%) of the title compound which was converted to the HCl salt, mp 215°–218° C.

EA: Calculated for C$_{22}$H$_{31}$N$_3$OS.2HCl.H$_2$O: C, 55.45; H, 7.40; N, 8.82 Found: C, 55.44; H, 7.17; N, 8.73

EXAMPLE 3

6-(4-Dibutylaminopropoxyphenyl)-5-methylimidazo[2,1-b]thiazole hydrochloride (Formula I: Het=thiazole; R$^1$,R$^2$=(CH$_2$)$_3$CH$_3$; m=3; R$^3$=CH$_3$)

The title compound was prepared as described in Example 1 starting with p-hydroxypropiophenone in the Example 1a procedure in the place of p-hydroxyacetophenone and using 2-aminothiazole (1.6 g, 16.4 mmol) in the Example 1c procedure in place of 2-amino-5-methyl-1,3,4-thiadiazole. The reaction sequence proceeded through α-bromo-4-chloropropoxypropiophenone and 6-(4-chloropropoxyphenyl)-5-methylimidazo[2,1-b]thiazole to yield 0.75 g (30%) of the title compound as the HCl salt, mp 210°–213° C.

EA: Calculated for C$_{23}$H$_{33}$N$_3$OS.2HCl.3/2HO: C, 55.30; H, 7.67; N, 8.14 Found: C, 55.24; H, 7.27; N, 8.60

EXAMPLE 4

6-(4-Dibutylaminopropoxyphenyl)imidazo[2,1-b]benzothiadihydrochloride (Formula I: Het=benzothiazole; R$^1$,R$^2$=(CH$_2$)$_3$CH$_3$; m=3; R$^3$=H)

The procedure of Example 1c was followed except that 2-aminobenzothiazole (4.2 g, 27.8 mmol) was used in the place of 2-amino-5-methyl-1,3,4-thiadiazole to yield 3-(4-chloropropoxyphenyl)imidazo[2,1-b]benzothiazole whic was then taken on according to the procedure of Example 1d to produce 1.96 g (69%) of the free base of the title compound which was converted to the HCl salt, mp 215°–217° C.

EA: Calculated for C$_{26}$H$_{33}$N$_3$OS.2HCl.H$_2$O: C, 59.30; H, 7.08; N, 7.98 Found: C, 59.39; H, 6.95; N, 7.92

EXAMPLE 5

2-(4-Dibutylaminopropoxyphenyl)imidazo[1,2-b]-1,2,4-triazine hydrochloride (Formula I: Het=1,2,4-triazine; R$^1$,R$^2$—(CH$_2$)$_3$CH$_3$; m=3; R$^3$=H)

The procedure of Example 1c was followed except that 3-amino-1,2,4-triazine (2.2 g, 23.2 mmol) was used in the place of 2-amino-5-methyl-1,3,4-thiadiazole to yield 3-(4-chloropropoxyphenyl)imidazo[1,2-b]-1,2,4-triazine which was then taken on according to the procedure of Example 1d to produce 0.34 g (58%) of the title compound as the HCl salt, mp 174°–177° C.

EA: Calculated for C$_{22}$H$_{31}$N$_5$O.HCl: C, 63.21; H, 7.72; N, 16.76 Found: C, 62.74; H, 7.49; N, 16.67

EXAMPLE 6

2-(4-Dibutylaminopropoxyphenyl)imidazo[1,2-a]pyrimidine dihydrochloride (Formula I: Het=pyrimidine; R$^1$,R$^2$=(CH$_3$)$_2$CH$_3$; m=3; R$^3$=H)

The procedure of Example 1c was followed except that 2-aminopyrimidine (2.2 g, 23 mmol) was used in the place of 2-amino-5-methyl-1,3,4-thiadiazole to yield 3-(4-chloropropoxyphenyl)imidazo[1,2-a]pyrimidine which was then taken on according to the procedure of Example 1d to produce 2.3 g (37%) of the free base of the title compound which was converted to the HCl salt, mp 154°–157° C.

EA: Calculated for $C_{23}H_{32}N_4O.2HCl.H_2O$: C, 58.59; H, 7.70; N, 11.88 Found: C, 58.77; H, 7.50; N, 11.99

EXAMPLE 7

2-(4-Dibutylaminopropoxyphenyl)-7-methylimidazo[1,2-a]pyrimidine trihydrochloride (Formula I: Het=methylpyrimidine; $R^1,R^2=(CH_2)_4CH_3$; m=3; $R^3=H$)

The procedure of Example 1c was followed except that 4-methyl-2-aminopyrimidine (1.9 g, 17.1 mmol) was used in the place of 2-amino-5-methyl-1,3,4-thiadiazole to yield 3-(4-chloropropoxyphenyl)-7-methyl-imidazo[1,2-a]pyrimidine which was then taken on according to the procedure of Example 1d to produce 2.2 g (81%) of the free base of the title compound which was converted to the HCl salt, mp 151°-154° C.

EA: Calculated for $C_{24}H_{34}N_4O.3HCl.H_2O$: C, 55.22; H, 7.53; N, 10.73 Found: C, 55.67; H, 7.49; N, 10.77

EXAMPLE 8 a. 2-Dimethylaminoamidinopyrimidine

To a solution of 2-aminopyrimidine (5.0 g, 52 mmol) in toluene (60 mL) was added dimethylformamide dimethylacetal (12.5 g, 0.11 mol) dropwise and the mixture was heated to reflux for 2 hr, concentrated and the resulting semi-solid was recrystallized from acetone-ether to give 8.0 g (100%) of the title amidine as a white solid.

$^1$H NMR (DMSO): δ 8.64 (s, 1H), 8.48 (d, J=4.8 Hz, 2H), 6.95 (t, J=4.8 Hz, 1H), 3.16 (s, 3H), 3.12 (s, 3H).

b. p-Hydroxybenzoylimidazo[1,2-a]pyrimidine

A mixture of the pyrimidine product of Example 8a (3.5 g, 23 mmol) and α-bromo-4-hydroxyacetophenone (5.0 g, 23 mmol) in ethanol (50 mL) was stirred at reflux for 3 hr. The mixture was cooled to RT and the resulting precipitate was collected by filtration and washed with cold ethanol to give the title product (3.4 g, 76%).

$^1$H NMR (DMSO): δ 9.73-8.76 (m, 2H), 8.19 (s,H), 7.62 (d, J=8.0 Hz, 2H), 7.26 (m, 1H), 6.16 (d, J=8.0 Hz, 2H).

c. 3-(4-Dibutylaminopropoxybenzoyl)imidazo[1,2-a]pyrimidine dihydrochloride (Formula II: Het=pyrimidine; $R^1,R^2=(CH_2)_3CH_3$; m=3; $R^4=H$)

To a mixture of the product of Example 8b (3.4 g, 10.7 mmol) in MeOH (10 mL) was added potassium hydroxide (1.6 g, 28.6 mmol) followed by dibutylaminopropyl chloride (5.9 g, 28.6 mmol). The mixture was stirred and heated to reflux for 36 hr and concentrated. The resulting oil was purified by flash chromatography (SiGel, 9:1 $CH_2Cl_2$—MeOH) to give the free base of the title compound. The HCl salt was prepared by dropwise addition of concentrated hydrochloric acid to a solution of the free base in MeOH, concentrated and recrystallized from acetone to yield 3.9 g (74%) of the title product as a white solid, mp 174°-177° C.

EA: Calculated for $C_{24}H_{32}N_4O_2.2HCl.H_2O$: C, 57.71; H, 7.27; N, 11.22 Found: C, 57.27; H, 6.94; N, 11.35

EXAMPLE 9 a. 2-Dimethylamidino-4-methylpyrimidine

The title compound was prepared according to the procedure of Example 8a substituting 2-amino-4-methylpyrimidine for 2-aminopyrimidine.

b. 3-(4-Dibutylaminopropoxybenzoyl)-7-methylimidazo[1,2-a]-pyrimidine hydrochloride The procedure of Example 8b was followed except that 2-dimethylamidino-4-methylpyrimidine (7.6 g, 46 mmol) was used in the place of 2-dimethylaminoamidinopyrimidine to produce p-hydroxybenzoyl-7-methylimidazo[1,2-a]-pyrimidine. This product was then reacted with dibutylaminopropyl chloride according to the procedure of Example 8c to produce 1.8 g (26%) of the free base of the title compound which was converted to the HCl salt, mp 168°-171° C.

EA: Calculated for $C_{25}H_{34}N_4O_2.HCl.3/2H_2O$: C, 61.77; H, 7.88; N, 11.53 Found: C, 61.84; H, 7.39; N, 11.54

What is claimed is:

1. An imidazo-fused heterocyclic compound of the following formula (II):

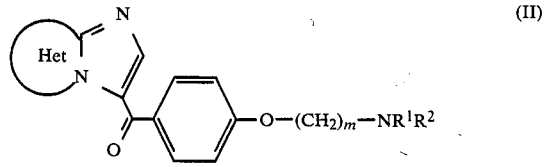

wherein
$R^1$ and $R^2$ are independently alkyl of 1 to 5 carbons;
m is an integer from 2 to 5; and
Het represents the atoms necessary to form an imidazo[2,1-b]thiazole ring system,
and the pharmaceutically acceptable acid-addition salts thereof.

2. The heterocyclic compound of claim 1, wherein $R^1$ and $R^2$ are independently methyl, ethyl, n-butyl or 3-methyl-n-butyl.

3. The heterocyclic compound of claim 1, wherein m is 3.

4. The heterocyclic compound of claim 1, wherein $R^1$ and $R^2$ are the same.

5. An anti-hypertensive or anti-anginal pharmaceutical composition which comprises a pharmaceutically effective amount of a heterocyclic compound of claim 1 in combination with a pharmaceutically-acceptable diluent or carrier.

6. A method for treating hypertension in a mammal which comprises administering to said mammal a pharmaceutical composition which comprises a pharmaceutically effective amount of a heterocyclic compound of the following formula (I) or (II) in combination with a pharmaceutically-acceptable diluent or carrier:

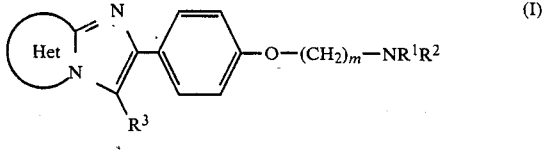

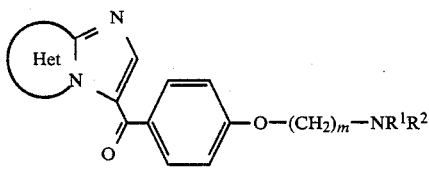

(II)

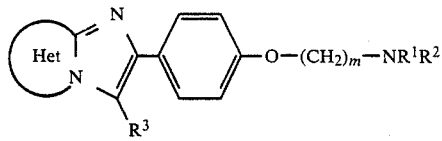

(I)

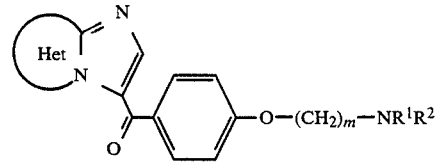

(II)

wherein
  R¹ and R² are independently alkyl of 1 to 5 carbons;
  R³ is hydrogen or alkyl of 1 to 5 carbons;
  m is an integer from 2 to 5; and
  Het represents the atoms necessary to form an imidazo[2,1-b]thiazole ring system,
and the pharmaceutically acceptable acid-addition salts thereof.

7. The method of claim 6, wherein
  R¹ and R² are independently methyl, ethyl, n-butyl or 3-methyl-n-butyl; and
  R³ is hydrogen, methyl, ethyl, n-butyl or 3-methyl-n-butyl.

8. The method of claim 6, wherein said compound is:
  6-(4-dibutylaminopropoxyphenyl)imidazo[2,1-b]thiazole, or
  6-(4-dibutylaminopropoxyphenyl)-5-methylimidazo[2,1-b]-thiazole.

9. The method of claim 6, wherein said compound is of the formula (I).

10. The method of claim 6, wherein said compound is of the formula (II).

11. The method of claim 6, wherein m is 3.

12. The method of claim 6, wherein R¹ and R² are the same.

13. A method for treating angina in a mammal which comprises administering to said mammal a pharmaceutical composition which comprises a pharmaceutically effective amount of a heterocyclic compound of the following formula (I) or (II) in combination with a pharmaceutically-acceptable diluent or carrier;

wherein
  R¹ and R² are independently alkyl of 1 to 5 carbons;
  R³ is hydrogen or alkyl of 1 to 5 carbons;
  m is an integer from 2 to 5; and
  Het represents the atoms necessary to form an imidazo[2,1-b]thiazole ring system,
and the pharmaceutically acceptable acid-addition salts thereof.

14. The method of claim 13, wherein
  R¹ and R² are independently methyl, ethyl, n-butyl or 3-methyl-n-butyl; and
  R³ is hydrogen, methyl, ethyl, n-butyl or 3-methyl-n-butyl.

15. The method of claim 13, wherein said compound is:
  6-(4-dibutylaminopropoxyphenyl)imidazo[2,1-b]thiazole, or
  6-(4-dibutylaminopropoxyphenyl)-5-methylimidazo[2,1-b]-thiazole.

16. The method of claim 13, wherein said compound is of the formula (I).

17. The method of claim 13, wherein said compound is of the formula (II).

18. The method of claim 13, wherein m is 3.

19. The method of claim 13, wherein R¹ and R² are the same.

* * * * *